United States Patent
Heilek et al.

(10) Patent No.: US 7,732,624 B2
(45) Date of Patent: Jun. 8, 2010

(54) PROCESS FOR OPERATING A CONTINUOUS REMOVAL OF A TARGET PRODUCT X IN THE FORM OF FINE CRYSTALS

(75) Inventors: Joerg Heilek, Bammental (DE); Ulrich Hammon, Mannheim (DE); Klaus Joachim Mueller-Engel, Stutensee (DE); Volker Schliephake, Schifferstadt (DE); Dieter Baumann, Speyer (DE)

(73) Assignee: BASF SE, Ludwigshafen (DE)

( * ) Notice: Subject to any disclaimer, the term of this patent is extended or adjusted under 35 U.S.C. 154(b) by 50 days.

(21) Appl. No.: 12/208,737

(22) Filed: Sep. 11, 2008

(65) Prior Publication Data

US 2009/0076286 A1    Mar. 19, 2009

Related U.S. Application Data

(60) Provisional application No. 60/971,994, filed on Sep. 13, 2007.

(30) Foreign Application Priority Data

Sep. 13, 2007    (DE) .................. 10 2007 043 759

(51) Int. Cl.
   *C07D 207/26* (2006.01)
   *C07C 51/43* (2006.01)
   *C07C 7/14* (2006.01)
(52) U.S. Cl. .................. 548/555; 562/600; 585/805
(58) Field of Classification Search ................ 548/555; 562/600; 585/805
   See application file for complete search history.

(56) References Cited

U.S. PATENT DOCUMENTS

| 6,939,991 | B2 | 9/2005 | Thiel et al. |
| 7,112,695 | B2 | 9/2006 | Eck et al. |
| 7,279,075 | B2 | 10/2007 | Thiel et al. |
| 7,393,436 | B2 | 7/2008 | Eck et al. |
| 2006/0199976 | A1 | 9/2006 | Heilek et al. |
| 2008/0183014 | A1 | 7/2008 | Diefenbacher et al. |

FOREIGN PATENT DOCUMENTS

| DE | 103 32 758 A1 | 5/2004 |
| DE | 103 00 816 A1 | 7/2004 |
| DE | 10 2005 009 890 A1 | 9/2006 |
| DE | 10 2007 004 960 A1 | 7/2008 |
| WO | WO 01/77056 A1 | 10/2001 |
| WO | WO 2004/035514 A1 | 4/2004 |

OTHER PUBLICATIONS

Research Disclosure Database No. 496005, Aug. 2005, 6 pages.
Research Disclosure Database No. 479008, 7 pages.

*Primary Examiner*—Kamal A Saeed
*Assistant Examiner*—Samantha L Shterengarts
(74) *Attorney, Agent, or Firm*—Oblon, Spivak, McClelland, Maier & Neustadt, L.L.P.

(57) ABSTRACT

A process for continuously removing a target product X in the form of fine crystals from a liquid phase P comprising the target product X and constituents other than the target product X by cooling suspension crystallization in an indirect heat transferer, in which the crystal suspension formed is conducted out of the heat transferer first into a mixed buffer tank and, from there, fed to an apparatus for separating the crystal suspension into crystals and liquid phase, and wherein external measures dissipate the oversaturation of the crystal suspension fed to the buffer vessel with target product X.

7 Claims, No Drawings

PROCESS FOR OPERATING A CONTINUOUS REMOVAL OF A TARGET PRODUCT X IN THE FORM OF FINE CRYSTALS

The present invention relates to a process for continuously removing a target product X in the form of fine crystals of the target product X from a liquid phase P consisting of the target product X and constituents $B_i$ other than the target product X, whose total mole fraction of constituents $B_i$ has the value $M_{B,P}^{tot}$, comprising the operation of an indirect heat transferer having a secondary chamber and at least one primary chamber, in which the secondary chamber and the at least one primary chamber are each spatially separated from one another by at least one material dividing wall which serves as a surface for transfer of heat out of the secondary chamber into the at least one primary chamber, by conducting a stream of liquid phase P into the secondary chamber of the heat transferer, while the at least one primary chamber is simultaneously flowed through by at least one fluid cooling medium such that, in the secondary chamber, fine crystals of the target product X form from the liquid phase P to leave a liquid residual phase R, and are suspended in the remaining liquid residual phase R which, compared to the liquid phase P, comprises the constituents other than the target product X with a total mole fraction $M_{B,R}^{tot} > M_{B,P}^{tot}$ and whose content of target product X is at least 70% by weight to obtain a suspension S of fine crystals of the target product X in the liquid residual phase R which has a degree of crystallization Y, and suspension S with the temperature $T_S^{out}$ is withdrawn continuously from the secondary chamber of the heat transferer, and further comprising the supply of suspension S withdrawn with the temperature $T_S^{out}$ to a mixed buffer vessel, and, with the aid of a pump, the charging of a separating apparatus from the buffer vessel with suspension of fine crystals of the target product X present in the buffer vessel, and the separation of the suspension supplied to the separating apparatus into crystals present therein and liquid phase present therein.

Processes for continuous crystallizative removal of a target product X from a liquid phase P comprising the target product X and constituents other than the target product X by a cooling suspension crystallization with the aid of a heat transferer (cooler or crystallizer) having a secondary chamber and at least one primary chamber are just as well known (cf., for example, DE-A 103 32 758, WO 2004/035514, Research Disclosure Database Number 496005 and 479008, and German application 10 2007 004 960.0) as the processes for separating the crystal suspension S formed in the former process into crystals and liquid phase, which generally follow this process. Such a separation can be undertaken, for example, by filtration, by screen centrifugation and/or in wash columns, as disclosed, for example, by WO 01/77056 and the prior art cited therein. Normally, an aforementioned separation also includes washing of the crystals removed in order to remove liquid phase adhering on the crystal surface. Such a wash can be effected, for example, with the melt of the crystals which have been removed beforehand and washed.

As a result of the transfer of heat from the liquid phase P which is fed to the secondary chamber and comprises the target product X through the material dividing wall (the heat transferer surface) which divides the secondary chamber and the at least one primary chamber from one another into the coolant flowing within the at least one primary chamber, the liquid phase P cools until the saturation limit of the liquid phase P with target product X is exceeded and the liquid phase P counteracts oversaturation by formation of crystals of the target product X.

The term "degree of crystallization" of a crystal suspension comprising fine crystals suspended in liquid phase means, in this document, the mass fraction or else proportion by mass of the fine crystals present in the crystal suspension in the total mass of the crystal suspension.

The degree of crystallization Y of the suspension S is thus calculated as the fraction of the crystal mass $m_{Kr,Y}$ present in suspension S at the degree of crystallization Y over the total mass $m_S$ of the suspension S:

$$Y = \frac{m_{Kr,Y}}{m_S}.$$

The degree of crystallization Y of the suspension S is thus necessarily between 0 and 1. The value "0" would correspond to an exclusively liquid phase, and the value 1 would correspond to an exclusively solid phase (i.e., in both cases, no suspension would be present any longer).

When a constituent $B_i$ is present in a liquid phase F (for example in the liquid phase P or in the liquid residual phase R) in the molar amount $n_i$ (the molar amount $n_i$ is calculated from the mass in which the constituent $B_i$ is present in the liquid phase F divided by the molar mass of the constituent $B_i$) and the target product X is present in the liquid phase F in the molar amount $n_x$ (the molar amount $n_x$ is calculated from the mass in which the target product X is present in the liquid phase P, divided by the molar mass of the target product X), the mole fraction $M_{B,F}^i$ of the constituent $B_i$ present in the liquid phase F is understood to mean the quotient of the number of moles $n_i$ divided by the sum formed from the number of moles $n_x$ and the total number of moles of all constituents $B_i$ other than the target product X which are present in the liquid phase F. In other words, $$M_{B,F}^i = \frac{^3 n_i}{n_x + \sum_{i=1}^{I} n_i},$$

assuming that the liquid phase F, as well as the target product X, comprises a total of I constituents $B_i$ different from the target product X and from one another.

When the liquid phase F is the liquid residual phase R or the liquid phase P, the "F" in $M_{B,F}^i$ should be replaced correspondingly by "P" or "R".

The total mole fraction $M_B^{tot}$ of the constituents $B_i$ other than the target product X which are present in the liquid phase F (for example in the liquid phase P or in the liquid phase R) is understood in this document to mean the sum of all individual values $M_{B,F}^i$ calculated for the particular constituents $B_i$.

Correspondingly, the mole fraction $M_X$ with which the target product X is present in the liquid phase F is defined as $$M_{X,F} = \frac{n_x}{n_x + \sum_{i=1}^{I} n_i}.$$

The relationship $M_{X,F} + M_{B,F}^{tot} = 1$ applies.

When the liquid phase F is the liquid residual phase R or the liquid phase P, the "F" in $M_{X,F}$ should be replaced correspondingly by "P" or "R".

A crystallizative removal of a target product X from a liquid phase P comprising the target product X and constituents other than the target product X is employed especially in order to remove the target product X from by-products formed in the course of its preparation. The target product X may already have been prepared directly by chemical reaction in the liquid phase.

However, the target product X may of course also have been prepared, for example, in the gas phase, from which the target product X is subsequently converted to the liquid phase, generally by condensative and/or absorptive measures, normally together with some secondary components accompanying the target product X in the gas phase. The crystallizative removal of the target product X can in principle be effected as a "sharp" thermal separating process directly from the liquid phase which is obtained as described in the course of preparation of target product X and comprises the target product X and secondary components.

Frequently, however, the aforementioned liquid phase, before employing a crystallizative removal of the target product X, will first be subjected to at least one "nonsharp" thermal separating process for the purpose of removing a portion of the aforementioned secondary components from the target product X.

A nonsharp separating process is defined as a separating process in which, from a thermodynamic point of view, the composition of the phase which forms when the separating process is employed and comprises enriched target product X is, in a thermodynamically necessary manner, markedly dependent on the composition of the mixture to be subjected to the separating process (cf., for example, McCabe-Thiele diagram). The nonsharp thermal separating processes include, for example, simple distillation, rectification, absorption, fractional condensation, desorption, extraction, stripping, azeotropic rectification, etc.

In contrast, crystallizative removal is a sharp thermal separating process in that the composition of the crystals which form, from a thermodynamic point of view, is very substantially independent of the composition of the liquid starting mixture (cf. also DE-A 10 2005 009 890 and DE-A 103 00 816).

The reason for the advantage of the nonsharp separating processes is generally that they can be operated with a high space-time yield. A disadvantage of nonsharp separating processes is, however, that the separating action achieved with them is comparatively limited.

A disadvantage of sharp separating processes is their normally comparatively limited space-time yield, but with normally very high separating action.

Against the above background, the two separating principles are therefore frequently also employed in the combined manner which follows.

First, at least one nonsharp thermal separating process is applied to the product mixture obtained in the course of preparation of the target product X to obtain liquid phase P which already comprises the target product X in enriched form compared to its proportion by weight in the product mixture. This liquid phase P which, as well as the target product X, still comprises secondary components other than the target product X is subsequently subjected to a crystallizative removal of the target product X, and the liquid residual phase R which remains (which is frequently also referred to as mother liquor), which comprises the secondary components in comparatively enriched form, is recycled at least partly into at least one of the nonsharp thermal separating processes employed beforehand. In this way, the advantages of the two separating principles can simultaneously be brought to bear.

In many cases, a liquid phase P which comprises a target product X and is subjected to a crystallizative removal of the target product X (and this also applies in the same way to the liquid phases P relevant in this application) therefore comprises at least two, in many cases at least three or four, frequently at least five or six and often at least seven or eight, or at least nine or ten, secondary components other than the target product X (such secondary components are present in the liquid phase P in the context of this application when they are detectable as a constituent thereof, for example by gas chromatography, liquid chromatography or by other means (for example such as water by Karl Fischer titration)).

In addition to by-products which are characteristic as a result of the preparation of the target product X, the liquid phase P comprising the target product X may, though, also comprise solvent or solvent mixture and/or assistants used in the course of for separation of the target product X from a reaction product mixture in the course of generation of the liquid phase P (for example absorbents, extractants, etc.). In other words, the liquid residual phase R may, for example, either be melts of the target product X and impurities, or solutions of target product X and solvents (or solvent mixtures), and also impurities in general.

The buffer vessel used in a process described at the outset of this document primarily pursues the purpose of increasing the flexibility in the preparation of target product X.

When, for example, the removal of the target product X in the indirect heat transferer becomes unavailable for a limited time owing to a fault, the production of target product X can nevertheless be continued continuously when the buffer vessel, to a certain degree, comprises a reservoir of crystal suspension of the target product X.

Frequently, a plurality of suspension crystallizers and a plurality of separating apparatus are also employed in parallel in the same way. When, for example, one of the separating apparatus operated in parallel becomes unavailable for a limited time owing to a fault, all suspension crystallizers can nevertheless continue to be operated when the capacity of, for example, a common buffer vessel is such that it is capable of accommodating the production stream of a suspension crystallizer for a limited time without having to pass it on to a separating apparatus.

When the number of suspension crystallizers operated in parallel is greater than the number of downstream separating apparatuses likewise operated in parallel, it is of course appropriate first to combine the crystal suspensions conducted out of the suspension crystallizers into a buffer vessel and then to distribute them from the buffer vessel to the separating apparatus operated in parallel.

Furthermore, in the case of suspension crystallizers operated in parallel, accompanying quality variations in the individual suspension crystallizer can be absorbed to a certain degree by feeding the crystal suspensions obtained in the individual suspension crystallizers to a common buffer vessel, in which they are mixed with one another and from which crystal suspensions are subsequently withdrawn for the purpose of their separation.

A disadvantage in the concept of intermediate buffering has, however, been found to be that the (crystal) suspension S withdrawn continuously from the secondary chamber of the heat transferer is normally not entirely in thermodynamic equilibrium, but rather still has an oversaturation of target product X to a limited degree.

When such (crystal) suspension S which is oversaturated in target product X in this way and has the temperature $T_s^{out}$ is conducted into the buffer vessel which is normally thermally insulated from its environment, the oversaturation is dissipated in the buffer vessel as a result of further crystal formation.

However, a disadvantage of crystal formation proceeding in the buffer vessel is that, in contrast to the suspension crystallization in the indirectly cooled heat transferer configured therefor, it proceeds in an uncontrolled manner.

This can lead, for example, to the growth of relatively large crystal agglomerates on the inner wall of the buffer vessel or, if the contents of the buffer vessel are mixed with a stirrer, on the stirrer, which become detached with increasing size and, for example, disrupt the smooth operation of the conveying of the crystal suspension present in the buffer vessel into the separating apparatus by means of the appropriate delivery pump, or in unfavorable cases can even completely prevent it.

The problem addressed by the present invention was therefore that of at least partly or entirely remedying the above problem.

Accordingly, a process is provided for continuously removing a target product X in the form of fine crystals of the target product X from a liquid phase P consisting of the target product X and constituents $B_i$ other than the target product X, whose total mole fraction of constituents $B_i$ has the value $M_{B,P}^{tot}$, comprising the operation of an indirect heat transferer having a secondary chamber and at least one primary chamber, in which the secondary chamber and the at least one primary chamber are each spatially separated from one another by at least one material dividing wall which serves as a surface for transfer of heat out of the secondary chamber into the at least one primary chamber, by conducting a stream of liquid phase P into the secondary chamber of the heat transferer, while the at least one primary chamber is simultaneously flowed through by at least one fluid cooling medium such that, in the secondary chamber, fine crystals of the target product X form from the liquid phase P to leave a liquid residual phase R, and are suspended in the remaining liquid residual phase R which, compared to the liquid phase P, comprises the constituents other than the target product X with a total mole fraction $M_{B,R}^{tot} > M_{B,P}^{tot}$ and whose content of target product X is at least 70% by weight to obtain a suspension S of fine crystals of the target product X in the liquid residual phase R which has a degree of crystallization Y, and suspension S with the temperature $T_S^{out}$ is withdrawn continuously from the secondary chamber of the heat transferer, and further comprising the supply of suspension S withdrawn (from the secondary chamber) with the temperature $T_S^{out}$ to a mixed buffer vessel, and, with the aid of a pump, the charging of a separating apparatus from the buffer vessel with suspension of fine crystals of the target product X present in the buffer vessel, and the separation of the suspension supplied to the separating apparatus into crystals present therein and liquid phase present therein, wherein, on the route from the secondary chamber into the buffer vessel, in the buffer vessel and/or in one or more pumped circulation lines (such pumped circulation lines can then also be used, for example, to keep the pumps which supply the separating apparatus with crystal suspension from the buffer vessel in operation when the separating apparatus becomes unavailable for a short time; in this way, settling of the crystals in the pump is counteracted) leading out of the buffer vessel and back into it, the temperature of the suspension S fed to the buffer vessel is increased with the aid of an external energy source to a value $T^{Pu}$ above $T_S^{out}$ and/or the total mole fraction of the constituents other than the target product X which are present in the liquid residual phase R of the suspension S fed to the buffer vessel is increased to a value $M_{B,Pu}^{tot}$ above $M_{B,R}^{tot}$ by external addition (from outside into the crystal suspension S) of constituents other than the target product X.

In general, $T^{Pu} - T_S^{out}$ will be $\geq 0.1$ K. In order, however, not to counteract the suspension crystallization carried out beforehand in the indirect heat transferer, $T^{Pu} - T_S^{out}$ will normally be $\leq 3$ K, preferably $\leq 2$ K and generally $\leq 1$ K. Frequently, $T^{Pu} - T_S^{out}$ will even be $\leq 0.7$ K or $\leq 0.5$ K.

In a corresponding manner, the increase from $M_{B,R}^{tot}$ to $M_{B,Pu}^{tot}$ (with $M_{B,R}^{tot}$ as the reference basis) will normally be $\geq 0.1\%$. In order, however, not to counteract the suspension crystallization carried out beforehand in the indirect heat transferer, the aforementioned increase will generally, however, be $\leq 5\%$, typically $\leq 3\%$ and usually $\leq 1\%$.

It will be appreciated that, in the process according to the invention, the increase from $T_S^{out}$ to $T^{Pu}$ and the increase from $M_{B,R}^{tot}$ to $M_{B,Pu}^{tot}$ can also be employed in combination. However, preference is given in accordance with the invention to carrying out the dissipation of the oversaturation present in the suspension S by a sole increase from $T_S^{out}$ to $T^{Pu}$.

The aforementioned temperature increase can be undertaken by means of direct and/or indirect energy, for example (heat) supply.

The term "external" means in this context that the heat of crystallization released in a dissipation of the oversaturation by further crystallization of the target product X is intended to be excluded as an energy or heat source.

Direct supply of energy, for example heat, is possible, for example, by metering substances whose temperature is above $T_S^{out}$ into the buffer vessel and/or into the feed line to the buffer vessel.

A useful substance of this kind is, for example, appropriately preheated target product X itself, preferably target product X which has been obtained beforehand in the course of an inventive removal. Alternatively, heated mixtures comprising target product X are useful for this purpose, the liquid phase P and liquid residual phase R being preferred mixtures of this kind. In principle, a useful mixture of this kind may also be acid water (cf., for example, WO 2004/035514, EP-A 1 818 324, DE-A 102 43 625, DE-A 103 23 758 and DE-A 10 2007 004 960).

It will be appreciated that, for the purpose of direct heat supply, it is also possible in a corresponding manner to meter in heated substances which correspond in terms of their substance type to an individual constituent $B_i$ or a mixture of several constituents $B_i$ which are present in any case in the liquid phase P as a result of its preparation. In principle, though, useful substances for direct heating are also appropriately heated substances which, in terms of their substance type, are not a constituent of the liquid phase P resulting from its preparation. Liquid residual phase R which has been removed beforehand from the suspension and heated appropriately is, for example, (as already stated) favorable for direct heating. What is important in the case of direct heat supply which is not effected as supply of appropriately heated target product X is that an increase of $M_{B,R}^{tot}$ automatically and simultaneously accompanies it. Advantageously in accordance with the invention, for the purpose of direct heating, preference will therefore be given to using substances whose molecular weight is less than three times the molecular weight, better less than twice the molecular weight and more preferably less than the molecular weight of the target product X (e.g. water).

The substances metered in for the purpose of direct heating preferably dissolve in the liquid residual phase R.

As already mentioned, the liquid phase obtained in the separation of the crystal suspension conducted out of the buffer vessel into crystals of the target product X present therein and liquid phase present therein, for the purpose of enhancing the yield of target product X, is advantageously recycled into the process for preparing the liquid phase P. This recycling is preferably effected into a nonsharp separating process used in many cases in the course of preparation of liquid phase P (cf., for example, FIG. 5 of WO 01/77056). It is therefore recommended, as the direct heat source to be used in accordance with the invention, to meter in substances which are either comparatively simple to remove from target product X in the course of the aforementioned nonsharp separating process, or substances which have a high (at least $\geq 5$, preferably $\geq 10$ and more preferably $\geq 15$) depletion coefficient $A^{Bi}$ in the course of the inventive crystallative removal of the target product X. The depletion coefficient $A^{Bi}$ is understood to mean the concentration ratio of concentration of the constituent $B_i$ remaining in the mother liquor (in the liquid residual phase R) in the inventive crystallizative removal of the target product X from the liquid phase P comprising it relative to concentration of the constituent $B_i$ remaining in the crystals (in each case expressed as % by weight based on the total amount of remaining mother liquor (or liquid residual phase R) or the total amount of crystals formed).

A removal of crystals/mother liquor to an extent of more than 90% by weight, preferably to an extent of more than 95% by weight, or 97, or 98, or 99% by weight of the total amount of mother liquor is generally sufficient to determine $A^{Bi}$ (the influence of the residual moisture content on the crystals is generally negligible). The aforementioned values for $A^{Bi}$ are preferably based on the combination of suspension crystallization and subsequent separation of the suspension S formed employed in the process according to the invention.

Direct supply of energy or heat is, however, for example, also possible by virtue of a resistance heater, for example an electrical resistance heater, being present in the buffer vessel, in the feed line to the buffer vessel or in a pumped circulation line, through which heat is introduced directly to the desired degree into the crystal suspension which has been supplied to the buffer vessel and/or is present in the buffer vessel. It will be appreciated that direct supply of energy can also be undertaken through injection of warm gases, or through the action of electromagnetic radiation (for example microwave radiation or infrared radiation).

Preferably in accordance with the invention, the energy or heat is supplied indirectly. For example, for this purpose, an externally trace-heated feed line (or a trace-heated pumped circulation line) can be employed to convey the crystal suspension into the buffer vessel.

However, very particular preference will be given to configuring the trace heating such that the buffer vessel is equipped with a jacket (alternatively, it is also correspondingly possible for fluid-conducting half-pipe coils or full-pipe coils to be applied (for example welded or laid) onto the buffer vessel wall), through whose interior a fluid heat carrier which has at least the desired target temperature for the contents of the buffer vessel is conducted. In principle, it is often sufficient when the bottom of the buffer vessel is double-walled or is equipped with half-pipe or full-pipe coils.

The buffer vessel or buffer tank is also, appropriately in application terms, equipped with a stirrer (advantageously a helical stirrer or another suspending stirrer) which mixes the crystal suspension present in the buffer vessel. Alternatively, for the purpose of mixing (and if appropriate simultaneously for the purpose of energy supply), an inert gas can also be conducted (sparged) through the crystal suspension.

However, it will be appreciated that the mixing can also be implemented by the mixing variants described in documents DE-A 10 2006 045 088 and DE-A 10 2006 045 089. The mixing can also be effected by pumped circulation. Useful fluid heat carriers for the aforementioned indirect trace heating are in principle the same materials which are recommended in this document as fluid cooling media for the suspension crystallizer.

Regarding the increase from $M_{B,R}^{tot}$ to $M_{B,Pu}^{tot}$, it is in principle also possible for constituents $B_i$ other than the target product X which have a temperature $\leq T_S^{out}$ to be metered in. Otherwise, the statements already made in connection with the direct heat supply for the increase from $T_S^{out}$ to $T^{Pu}$ apply.

The preferred construction material for the buffer tank is stainless steel, owing to its favorable thermal conductivity. Preferred stainless steels are those of DIN material numbers 1.4541 and 1.4571. The wall thickness is typically from 3 to 30 mm.

(Crystal) suspension S is withdrawn from the secondary chamber advantageously under overflow control with the aid of a height-adjustable overflow weir. However, it can also be effected under level control through an immersed tube.

Both the suspension crystallizer and the buffer tank and separating apparatus are normally operated with both thermal insulation and steam sealing by virtue of thermal insulation materials (e.g. Styropo®) applied to their shell and steam barriers adhesive-bonded to these (e.g. Alu-Butyl foil from WeGo Systembaustoffe, VTI branch in D-67014 Ludwigshafen/Rhein).

Useful pumps for charging the separating apparatus with crystal suspension conducted out of the buffer tank are in principle delivery pumps of any kind. Advantageously in accordance with the invention, radial centrifugal pumps are used. Among these, those recommended in DE-A 103 53 014 are advantageous. Among these circulation pumps, those of the Kanalrad type are particularly favorable. The quantitative control is normally effected through speed regulation of the pumps.

The delivery motion of the fluid phase present in the secondary chamber of the indirect heat transferer (of the suspension crystallizer) through said heat transferer is in many cases already sufficient to cause suspension of the crystals of the target product X removed in the secondary chamber.

In general, the secondary chamber, however, additionally has one or more mixing apparatuses. This may in the simplest case be sparging with an auxiliary gas (e.g. air), one or more stirrers, a wiping apparatus for keeping the dividing wall between secondary chamber and primary chamber free from crystals and/or pumped circulation. The delivery of the mass flow fed to the secondary chamber through said chamber is normally accomplished by forcing the liquid phase P into the secondary chamber with the aid of pumps.

For the performance of the process according to the invention, all kinds of indirect heat transferers are useful in principle (by definition, they have the primary chamber/secondary chamber structure required in accordance with the invention) (cf.: for example, Kristallisation, Grundlage und Technik [Crystallization, fundamentals and technology], Günther Metz, Springer-Verlag, Berlin 1969, p. 214 ff, and Ullmanns Encyclopädie der technischen Chemie, Verfahrenstechnik I [Process technology I], Verlag Chemie Weinheim, 4th edition, 1972, page 672-682, and the prior art mentioned in these standard works).

Preferably in accordance with the invention, the indirect heat transferer used will be one in which the side of the at least one dividing wall which separates the at least one primary chamber from the secondary chamber in each case which faces the secondary chamber is operated with wiping (continuous scraping of the relevant heat-transferring surface with the aid of suitable wiping apparatus). Such indirect heat transferers (crystallizers, coolers) are frequently also referred to as scraped-surface coolers. The at least one primary chamber in the indirect heat transferer may be introduced so as to be either immobile or mobile (for example removable cooling disks). In the latter case, the mobile primary chamber elements can be exchanged from time to time.

As an illustrative selection, the following can be used as suspension crystallizers for the process according to the invention:

rotary tube crystallizers (the secondary chamber is the tube interior; the tube shell is a jacket within which the coolant is conducted in cocurrent or in countercurrent to the mass flow inside the tube; the tube interior is preferably slightly tilted from the horizontal; crystal crusts which may form on the tube interior wall can continuously be knocked off (for example with chains) and/or scraped off (e.g. with radial wipers); the liquid phase P is fed continuously into one end of the tube; the suspension S is conducted out continuously at the other end of the tube);

a vessel with hung cooling elements (cooling elements (e.g. cooling disks) are hung in an unstirred vessel; the liquid phase P is, for example, conducted into the vessel bottom left, and the suspension S is conducted out of the vessel under overflow control top right; cooling elements having encrustations are replaced by fresh cooling elements);

stirred vessels (these are, for example, vessels which are surrounded by a cooling jacket and/or equipped with cooling elements (cooling coils, cooling disks); in addition, they have a stirrer which mixes the contents of the interior not occupied by the cooling elements continuously by stirring; the liquid phase P is fed in by pumps and the suspension S is conducted out by overflow);

votator (jacket-cooled tube at rest, whose wall is scraped by flat scraping blades pressed on with springs; the liquid phase P is pumped in at one end, the suspension S flows out at the other end);

pan crystallizer (trough-like vessel with horizontal shaft on which are mounted, at regular intervals, hollow pans (hollow disks) which are flowed through by the cooling medium generally in countercurrent to the crystallizing liquid phase P and which have sector-shaped cutouts for the passage of liquid phase P or crystal suspension; gentle stirring of the crystal suspension through the pans and the coolant lines connecting them; the liquid phase P is conducted into the pan crystallizer on one side by pumps and conducted out of the pan crystallizer under overflow control on the opposite side);

forced-circulation crystallizer from Swenson or Messo Chemietechnik.

Crystallizers particularly suitable for the process according to the invention (especially in the case of acrylic acid, methacrylic acid, p-xylene or N-vinylpyrrolidone as target product X) are cooling disk crystallizers (cooling disks present in the secondary chamber comprise the primary chambers), for example those disclosed in Research Disclosure Database Number 496005 (published in August 2005) and in Research Disclosure Database Number 479008 (published in March 2004).

The fluid coolants (or assistants) used may be either gases or liquids.

Preference is given in accordance with the invention to using liquid coolants (or heating media). Useful such liquid coolants (or heating media) include, for example, heat carrier oils, water, solutions of salts in water, mono- or polyhydric organic alcohols such as methanol, ethanol, propanol, glycol and/or glycerol, but also mixtures of one or more of the aforementioned coolants, for example water/methanol mixtures or water/glycol mixtures (for example with from 10 to 60% by weight of glycol).

The temperature $T_K^{in}$ (the temperature with which the fluid cooling medium is fed to the at least one primary chamber) is set in an inventive cooling crystallization typically from 0 to 20 K, often from 1 to 15 K and usually from 2 to 10 K below $T_S^{out}$ (that temperature with which the suspension S is withdrawn from the secondary chamber). $T_K^{in}$ is necessarily below that temperature with which the liquid phase P is simultaneously fed to the secondary chamber of the heat transferer.

In many cases, however, there remain dividing wall surface elements which can be wiped only with difficulty, if at all. This is, for example, the case when the primary chamber is the interior of a circular cooling disk which is present, for example, immersed in a simple manner into the liquid phase flowing within the secondary chamber. While the front side and the back side of the cooling disk are amenable to wiping in a comparatively simple manner, this is not normally the case for the outer surface of the cooling disk. Such surface elements are therefore generally subjected to trace heating which is intended to suppress their encrustation with crystals. Such trace heating may, for example, be resistance trace heating. It will be appreciated that such trace heating can, though, also be implemented by indirect heat exchange (for example flow of a fluid heating medium through a mounted hollow profile).

The crystals of the suspension crystals which form in the course of performance of the process according to the invention typically have a longitudinal dimension (longest direct line connecting two points on the crystal surface) in the range from 1 to 10 000 μm, often from 10 to 1000 μm, frequently from 100 to 800 μm and in many cases from 300 to 600 μm.

Otherwise, the crystallizative removal can be carried out like the suspension crystallizations performed in the prior art.

The increase from $T_S^{out}$ to $T^{Pu}$ and/or from $M_{B,R}^{tot}$ to $M_{B,Pu}^{tot}$ will generally be undertaken in the context of the present invention only to the degree as required for the dissipation of the oversaturation in the suspension S. Otherwise, the effect of the suspension crystallization would be counteracted to a certain degree.

The process according to the invention is suitable when the content in the liquid residual phase R (mother liquor) present in the suspension S withdrawn from the secondary chamber of target product X is >70% by weight. However, it is also suitable when the aforementioned content of target product X in the liquid residual phase R is ≧80% by weight, or ≧85% by weight, or ≧87% by weight, or ≧90% by weight, or ≧92% by weight, or ≧94% by weight, or ≧95% by weight, or ≧96% by weight, or ≧97% by weight, or ≧98% by weight, or ≧99% by weight.

In other words, the process according to the invention is suitable in the case of those liquid phases P whose content of target product X is >70% by weight, or ≧75% by weight, or ≧80% by weight, or ≧85% by weight, or ≧87% by weight, or ≧90% by weight, or ≧92% by weight, or ≧94% by weight, or ≧95% by weight, or ≧96% by weight, or ≧98% by weight, or ≧99% by weight. In general, the aforementioned content in the liquid phase P fed to the secondary chamber of the heat transferer in the process according to the invention of target product X will, however, be ≦99.995% by weight, usually ≦99.99%.

Useful target product X for the suspension crystallization performed as a cooling crystallization in accordance with the invention are, for example, saturated or unsaturated carboxylic acids such as acetic acid, propionic acid, acrylic acid and methacrylic acid, or substituted aromatics (with, for example, halogens, methyl, carboxyl, hydroxyl and/or nitrogen groups (e.g. —$NH_2$) as substituents) such as p-xylene, cresol and chlorobenzene, or polycyclic aromatic compounds such as naphthalene and bisphenol A, or isocyanates such as TDI and MDI, or vinyl compounds such as N-vinylpyrrolidone, or formaldehyde oligomers such as trioxane or inorganic salts such as sodium or potassium salts (e.g. the sulfates, chlorides, bromides and iodides).

In particular, the process according to the invention is suitable in the case of acrylic acid, methacrylic acid, p-xylene or N-vinylpyrrolidone as the target product X.

When acrylic acid is the target product X, for example, water, diacrylic acid (Michael adducts), methacrylic acid, benzoic acid, acetic acid and propionic acid are substances suitable in accordance with the invention for increasing $M_{B,R}^{tot}$ to $M_{B,Pu}^{tot}$ by external addition. Advantageously in accordance with the invention, in the case of acrylic acid as the target product X, for the purpose of the aforementioned increase from $M_{B,R}^{tot}$ to $M_{B,Pu}^{tot}$, it is also possible to use so-called acid water, as is normally obtained in the course of a removal of acrylic acid from the product gas mixture of a heterogeneously catalyzed partial gas phase oxidation of a $C_3$ precursor compound of acrylic acid (e.g. propane, propylene, acrolein, propionic acid, propanol, glycerol and/or propionaldehyde) (cf., for example, WO 2004/035514, German application 10 2007 004 960.0, DE-A 102 43 625 and DE-A 103 23 758). In general, acid water comprises at least 60% by weight (frequently at least 70% by weight, usually at least 75% by weight, in many cases at least 80% by weight) of water, and at least 3% by weight (frequently at least 5% by weight, often at least 7% by weight, in many cases at least 9% by weight or at least 11% by weight) of acrylic acid.

When methacrylic acid is the target product X, for example, water, acrylic acid and acetic acid are substances suitable in accordance with the invention for increasing $M_{B,R}^{tot}$ to $M_{B,Pu}^{tot}$ by external addition.

When p-xylene is the target product X, for example, water and m- and o-xylene are substances suitable in accordance with the invention for increasing $M_{B,R}^{tot}$ to $M_{B,Pu}^{tot}$ by external addition.

When N-vinylpyrrolidone (also 1-vinyl-2-pyrrolidone) is the target product X, for example, water and 2-pyrrolidone are substances suitable in accordance with the invention for increasing $M_{B,R}^{tot}$ to $M_{B,Pu}^{tot}$ by external addition.

The process according to the invention is very particularly suitable in the case of acrylic acid as the target product X and of crude acrylic acid as liquid phase P which has, for example, one of the following contents:

| | |
|---|---|
| >70% by weight of | acrylic acid, |
| up to 15% by weight of | acetic acid, |
| up to 5% by weight of | propionic acid, |
| up to 5% by weight of | low molecular weight aldehydes, |
| up to 3% by weight of | polymerization inhibitors, |
| 0 to 5% by weight of | diacrylic acid (Michael adduct), and |
| up to 25% by weight of | water; |
| or | |
| ≧80% by weight of | acrylic acid, |
| ≧100 ppm by weight to ≦15% by weight of | acetic acid, |
| ≧10 ppm by weight to ≦5% by weight of | propionic acid, |
| up to 5% by weight of | low molecular weight aldehydes, |
| up to 3% by weight of | polymerization inhibitors and |
| 0 to 5% by weight of | diacrylic acid (Michael adduct), and |
| up to 15% by weight of | water; |
| or | |
| ≧85% by weight of | acrylic acid, |
| ≧100 ppm by weight to ≦10% by weight of | acetic acid, |
| ≧10 ppm by weight to ≦5% by weight of | propionic acid, |
| up to 5% by weight of | low molecular weight aldehydes, |
| up to 3% by weight of | polymerization inhibitors, |
| 0 to 5% by weight of | diacrylic acid (Michael adduct), and |
| up to 10% by weight of | water; |
| or | |
| ≧90% by weight of | acrylic acid, |
| ≧100 ppm by weight to ≦5% by weight of | acetic acid, |
| ≧10 ppm by weight to ≦2% by weight of | propionic acid, |
| up to 2% by weight of | low molecular weight aldehydes, |
| up to 2% by weight of | polymerization inhibitors, |
| 0 to 3% by weight of | diacrylic acid (Michael adduct), and |
| up to 9% by weight of | water; |
| or | |
| ≧95% by weight of | acrylic acid, |
| ≧100 ppm by weight to ≦3% by weight of | acetic acid, |
| ≧10 ppm by weight to ≦2% by weight of | propionic acid, |
| up to 2% by weight of | low molecular weight aldehydes, |
| up to 2% by weight of | polymerization inhibitors, |
| 0 to 2% by weight of | diacrylic acid (Michael adduct), and |
| up to 4.9% by weight of | water; |
| or | |
| 93 to 98% by weight of | acrylic acid, |
| 1 to 5% by weight of | water, |
| 0.001 to 3% by weight of | acrolein, |
| ≧0 to 3% by weight of | methacrolein, |
| ≧0 to 3% by weight of | methacrylic acid, |
| 0.1 to 3% by weight of | acetic acid, |
| 0.01 to 3% by weight of | propionic acid, |
| 0.001 to 3% by weight of | formaldehyde, |
| 0.001 to 3% by weight of | aldehydes other than formaldehyde, |
| 0.01 to 3% by weight of | maleic acid, and |
| ≧0 to 3% by weight of | protoanemonin. |

Crude acrylic acids are obtainable, for example, by the known prior art processes (cf., for example, EP-A 1 818 324, WO 01/77056, DE-A 103 32 758, DE-A 102 43 625, German application 10 2006 057 631.4, German application 10 2006 062 258.8, German application 10 2007 004 960.0, WO 2004/035514, German application 10 2006 049 939.5, DE-A 10 2005 029 629, WO 03/041832 and DE-A 10 2005 015 639 and also the prior art cited in these documents).

These are generally crude acrylic acids which are obtained (derived) from the product gas mixture of a heterogeneously catalyzed partial oxidation of at least one $C_3$ precursor compound of acrylic acid (e.g. propane, propylene, glycerol, acrolein, propionic acid, propanol and/or propionaldehyde).

For the process according to the invention, a useful crude acrylic acid for obtaining the liquid phase P is especially one which has been obtained from the product gas mixture of a heterogeneously catalyzed partial gas phase oxidation of at least one $C_3$ precursor compound using at least one nonsharp separating process. This is especially true when the liquid phase obtained in the inventive separation is recycled at least partly into at least one nonsharp separating process used to prepare the crude acrylic acid from the product gas mixture of the gas phase partial oxidation.

The basic structure of such a combined use of nonsharp separating processes and the sharp separating process of crystallization is taught, for example, by DE-A 196 06 877, EP-A 792 867, and also EP-A 1 484 308, EP-A 1 116 709, EP-A 1 818 324, and especially EP-A 1 015 410.

In the simplest case, the crude acrylic acid to be used to obtain the liquid phase P may be the absorbate and/or partial condensate and/or condensate obtained by fractionation from an absorptive and/or condensative removal of acrylic acid from the product gas mixture of a heterogeneously catalyzed partial gas phase oxidation of at least one of the $C_3$ precursors listed in this document. The liquid phase obtained in the inventive separation is then appropriately recycled into the absorption and/or condensation (cf. EP-A 1 818 324).

Advantageously, the acrylic acid present as the target product X in liquid phase P is based on a partial oxidation product gas mixture which comprises:

1 to 30% by volume of acrylic acid,
$\geq 0$ to or 0.005 to 10% by volume of propylene,
$\geq 0$ or 0.001 to 2% by volume of acrolein,
$\geq 0$ or 0.001 to 2% by volume of methacrolein,
$\geq 0$ or 0.001 to 2% by volume of methacrylic acid,
$\geq 0$ or 0.005 to 10% by volume of molecular oxygen,
$\geq 0$ or 0.005 to 3% by volume of acetic acid,
$\geq 0$ or 0.001 to 2% by volume of propionic acid,
$\geq 0$ or 0.001 to 2% by volume of formaldehyde,
$\geq 0$ or 0.001 to 2% by volume of other aldehydes,
and 10 to 98 or 50 to 98% by volume of (inert) diluent gases.

The diluent gases may, for example, comprise:
$\geq 0$ or 0.005 to 90% by volume of saturated $C_1$-$C_6$-hydrocarbons (especially propane, methane and/or ethane),
$\geq 0$ or 0.05 to 30% by volume of steam,
$\geq 0$ or 0.05 to 15% by volume of carbon oxides (CO and/or $CO_2$),
and $\geq 0$ or 1 to 90% by volume of molecular nitrogen.

The partial oxidation product gas mixture may be derived especially from a partial oxidation as described in documents DE-A 10 2004 032 129 and their equivalent foreign patents, DE-A 10245585, WO 03/076370, WO 01/96271, EP-A 117 146, WO 03/011804, U.S. Pat. No. 3,161,670, DE-A 33 13 573, DE-A 103 16 039 and WO 01/96270, proceeding from propylene and/or propane, and, as a propylene source, may have a propane dehydrogenation and/or oxdehydrogenation (if appropriate under heterogeneous catalysis) as a preceding reaction stage.

To separate the crystal suspension fed from the buffer vessel to the separating apparatus into crystals present therein and liquid phase present therein, useful processes in the process according to the invention are quite generally all of those detailed in documents WO 2006/111565, WO 01/77856, WO 02/055469 and WO 03/078378 (for example mechanical separating processes such as centrifugation). Advantageously, the apparatus is a wash column with forced transport of the separated crystals (e.g. acrylic acid crystals). The proportion by volume of crystals in the crystal bed generally reaches values of >0.5. In general, the wash column is operated at values of from 0.6 to 0.75. The wash liquid used is advantageously the melt of crystals purified (removed) beforehand in the wash column (for example acrylic acid crystals). The washing is normally effected in countercurrent.

More particularly, the process according to the invention comprises those processes in which the liquid phase P has >70% by weight, or $\geq 75$% by weight, or $\geq 80$% by weight, $\geq 85$% by weight of acrylic acid, or $\geq 90$% by weight of acrylic acid, or $\geq 95$% by weight of acrylic acid.

In addition, it is advantageous in accordance with the invention when the water content of the acrylic acid, as the liquid phase P comprising the target product X, based on acrylic acid present in the liquid phase P, is from 0.2 or 0.4 to 8, or to 10, or to 20, or to 30% by weight, or from 0.60 to 5% by weight, or from 0.60 to 3% by weight.

Of course, the process according to the invention can also be applied to all crude acrylic acids of WO 98/01414, and also to all crude p-xylenes of EP-A 097 405, as the liquid phase P.

In general, the temperature of the (crystal) suspension S when it is withdrawn from the secondary chamber ($T_S^{out}$) in the case of use of crude acrylic acid as the liquid phase P comprising the target product X in the process according to the invention is in the range from −25° C. to +14° C., especially in the range from −5° C. to +12° C. and particularly advantageously in the range from 4 or from 6 to 9° C.

It will be appreciated that all process steps in which acrylic acid is involved are carried out with inhibition of polymerization. The procedure may be as described in the prior art. A prominent position among the entirety of the acrylic acid process stabilizers available is taken by dibenzo-1,4-thiazine (PTZ), 4-hydroxy-2,2,6,6-tetra-methylpiperidine 1-oxyl (4-OH-TEMPO) and p-methoxyphenol (MEHQ), which may each be part of liquid phase P (for example of the crude acrylic acid) alone, in pairs or as a three-substance mixture. Typically, their total amount based on acrylic acid present in the liquid phase P is from 0.001 to 2% by weight.

In a manner corresponding to that explained by way of example for acrylic acid, it is also possible to integrate the process according to the invention into the preparation process of other target products X.

In particular, the present invention therefore comprises processes in which the buffer vessel, as a separating apparatus with crystal suspension present in the buffer vessel, is used to charge a wash column which has a wash column wall which surrounds a process chamber,
liquid phase is released from the process chamber while retaining the crystals present in the crystal suspension to form a crystal bed in the process chamber from the crystal suspension conducted into the process chamber,
the crystal bed is conveyed within the process chamber,
at least one force other than gravity acts in the process chamber in the conveying direction of the crystal bed and conveys the crystal bed within the process chamber,
pure melt which consists of molten crystals which have been removed beforehand by this wash column separation process is conducted within the process chamber in countercurrent to the crystal bed such that a wash front which divides the crystal bed into a liquid phase zone and into a pure melt zone forms in the crystal bed, and
crystals in solid and/or molten form which have been washed in the wash column are discharged continuously at the opposite end of the wash column to the feed of the crystal suspension.

The aforementioned is true in particular when the target product X in the process according to the invention is acrylic acid. In general, in this case, the removal of the fine acrylic acid crystals is followed by a further process in which acrylic acid crystals removed are melted and subjected to a polymerization (preferably a free-radical polymerization) with themselves or with other, at least monoethylenically unsaturated compounds (for example to a solution polymerization, emulsion polymerization, suspension polymerization, gas phase polymerization, or bulk polymerization). Such a process may also follow when the separation of the crystal suspension into crystals and liquid phase is undertaken in a different manner than that with a wash column.

In general, in the process according to the invention, the mass flow of liquid phase P fed to the secondary chamber of an indirect heat transferer will be from 2 to 80 t/h. This corresponds to mass flows $\dot{m}_x$ fed to the secondary chamber as a constituent of liquid phase P of from 1.4 to 79.8 t/h.

Depending on the particular separating problem (including the separating apparatus used) and the type and size of the crystals which constitute the crystal assembly, the degree of crystallization Y of the suspension S is frequently within the range from 0.10 to 0.50, with greater frequency in the range from 0.20 to 0.40, and it is particularly frequently from 0.25 to 0.35 or 0.30.

EXAMPLE AND COMPARATIVE EXAMPLE

I. Example

Two identical stirred and wiped cooling disk crystallizers of the design described in Research Disclosure Database Number 496005 (published in August 2005) were operated in parallel. These were each a trough in which 24 wiped circular cooling plates (cooling disks) at an equidistant interval of 30±1 cm were arranged hung in succession. The plate diameter was 3.3 m. The plate thickness was 5.2 cm.

The coolant used for each of the two crystallizers was a mixture of 70% by weight of water and 30% by weight of glycol. The coolant was conducted through the crystallizer in countercurrent to the liquid phase P fed to the crystallizer in the particular crystallizer, and passed on from cooling disk to the next cooling disk but one. In other words, the coolant in each of the two crystallizers was conducted divided in the form of two equal and parallel streams through the cooling plates of the particular crystallizer. Half of the stream led through the numerically even cooling plates; the other half of the stream led through the numerically odd cooling plates (numbering of the cooling disks in flow direction of the coolant beginning with 1). The cooling areas were manufactured from stainless steel (DIN material 1.4541). The wall thickness of the stainless steel cooling areas was 4 mm. The rotation speed of the wipers was from 5 to 6 revolutions per minute. The shaft conducted through the center of the cooling disks, which drives the wipers, was sealed with water-flushed stuffing box packings (packing threads made of Teflon; flush rate=a few liters per hour up to a few 10 s of l/h per seal). On the circumference of each cooling disk, where it is not possible to wipe, a hollow profile was mounted (a tube welded on; (material: stainless steel (DIN material 1.4541), wall thickness 3.6 mm)). For the purpose of trace heating the individual cooling disks of a crystallizer, a liquid heating medium I flowed in parallel in to the hollow profile thereof, which was likewise composed of 70% by weight of water and 30% by weight of glycol.

The wipers were segmented in the radial direction (4 segments).

The specific pressing force of the wipers in the installed state at right angles to the cooling surface was about 4 N per cm of active wiping edge length. The wiper material used was Multilene® PE 1000. In addition to the wipers, the shaft drove paddles (between two cooling disks and before the first and last cooling disk, in each case in symmetrical arrangement), which brought about improved mixing. In the back part of the particular crystallizer in conveying direction of the crystal suspension (beyond the last cooling disk), the (crystal) suspension S formed in the individual crystallizer in each case flowed over an overflow weir into a buffer tank stirred with a helical stirrer (made of stainless steel of DIN material No. 1.4541; internal volume: 20 m$^3$; wall thickness: 10 mm; internal diameter=2.58 m; the bottom of the buffer vessel was designed with a welded-on half-pipe coil; the liquid heating medium II conducted through the half-pipe coil space was a mixture of 70% by weight of water and 30% by weight of glycol; the steady-state fill contents of the buffer tank of crystal suspension was 16 m$^3$), from which two identical hydraulic melt wash columns were charged in parallel with crystal suspension withdrawn from the buffer tank (separation of the mass flow of suspension S withdrawn from the buffer tank (the strength of the withdrawal flow corresponded to the strength of the total feed stream from the crystallizers) between the two wash columns was followed in each case, before entry into the particular wash column, by flow through a coriolis mass flow meter for the purpose of determining the degree of crystallization Y via the mass density of the particular partial mass flow) for the purpose of separating it into liquid phase and crystals. The separation in the melt wash columns was effected as described in documents EP-A 1 272 453, EP-A 1 448 283, WO 03/041833, EP-A 1 305 097, DE-A 101 56 016, DE-A 10 2005 018702, DE-A 102 23 058 and German application 10 2007 004 960.0. The internal diameter of the individual wash column was 1.4 m. The wash columns were charged with crystal suspension in each case by means of a centrifugal pump (Kanalrad type, from KSB), and the flow was controlled by means of speed regulation of the pumps. The liquid phase removed in the wash columns was recycled via a further buffer vessel as described in FIG. 5 of WO 01/77056 or as described in German application 10 2007 004 960.0 into the fractional condensation used to prepare the liquid phase P comprising acrylic acid as the target product.

Each of the two crystallizers had a roof (stainless steel (DIN material 1.4541)) and was sealed against ingress of ambient air. Both the wash columns, which were likewise manufactured from stainless steel (DIN material 1.4541, wall thickness 10 mm), and the crystallizers and the buffer tank were thermally insulated and provided with a steam barrier by means of Styropor applied to their stainless steel shell and Alu-Butyl foil from WeGo Systembaustoffe, VTI branch in 67014 Ludwigshafen/Rhein, applied thereto (cf., for example, DE-A 10 2007 032 633).

The wash columns, the buffer tank and the crystallizers were accommodated in a common housing. The air temperature in the overall housing was between 25° C. and 28° C. The mass transfer from the crystallizers into the buffer tank and from there into the wash column was effected likewise sealed from the ambient air, and also with heat insulation and a steam barrier. The degree of crystallization Y was set independently to 0.28 for each of the two crystallizers operated in parallel. A closed-loop control deviation was counteracted in both cases by increasing or decreasing the particular $T_K^{in}$.

The operating state of the two crystallizers was characterized by the following boundary conditions:

target product X=acrylic acid.

Phase P fed to the crystallizers=crude acrylic acid which derived from a fractional condensation of a product gas mixture of a two-stage heterogeneously catalyzed partial gas phase oxidation of chemical-grade propylene to acrylic acid. Its content of acrylic acid was 94.44% by weight. $M_{B,P}^{tot}$ was 0.1483.

The entrance temperature of the coolant into the primary chamber region of the particular crystallizer $T_K^{in}$ was approx. 2.1° C.

The exit temperature of the coolant from the primary chamber region of the particular crystallizer $T_K^{out}$ was approx. 4.7° C.

The coolant mass flow $\dot{m}_K$ fed to the primary chamber of the particular crystallizer was approx. 208 t/h.

The entrance temperature of the heating medium into the particular hollow profile of the cooling disks of the particular crystallizer $T_{H,I}^{in}$ was approx. 12° C.

The exit temperature of the heating medium I from the particular hollow profile of the cooling disks of the particular crystallizer $T_{H,I}^{out}$ was approx. 10.4° C.

The total heating medium mass flow I $\dot{m}_{H,I}$ fed to the hollow profiles of the cooling disks of the particular crystallizer was approx. 43 t/h.

The entrance temperature of liquid phase P into the particular secondary chamber, $T_P^{in}$, was approx. 14° C.

The temperature of the suspension S when it was withdrawn from the particular secondary chamber $T_S^{out}$ was approx. 7.0° C.

The acrylic acid content of the liquid residual phase R in the suspension S withdrawn from the secondary chamber was 92.34% by weight.

The total mole fraction $M_{B,R}^{tot}$ of the constituents other than acrylic acid in the aforementioned liquid residual phase R was 0.1991.

The mass flow $\dot{m}_P$ with which the liquid phase P was fed to the secondary chamber of the particular crystallizer and the suspension S was conducted out of the secondary chamber of the particular crystallizer was approx. 26.5 t/h. This gave rise to an $\dot{m}_x$ of approx. 25.0 t/h for each secondary chamber.

The entrance temperature of the heating medium II into the half-pipe coil space of the buffer tank bottom $T_{H,II}^{in}$ was approx. 32° C. The exit temperature of the heating medium II from the half-pipe coil space of the buffer tank bottom $T_{H,II}^{out}$ was approx. 26° C. The total heating medium mass flow II fed to the half-pipe coil space of the buffer tank bottom was approx. 5 t/h.

The temperature $T^{Pu}$ of the crystal suspension present in the buffer tank was 7.7° C.

The above-described operating state was maintained with customary variations as described above over a period of two weeks without difficulty. The dissipation of the oversaturation was maintained continuously.

II. Comparative Example

The procedure was as in the example, except that the heating medium stream II was not fed to the half-pipe coil space of the buffer tank bottom.

Instead, the closed half-pipe coil space of the buffer tank bottom comprised standing fluid heating medium II. The temperature of the crystal suspension present in the buffer tank corresponded essentially to the temperature of the suspension S when it was withdrawn from the particular secondary chamber $T_S^{out}$. There was no dissipation of oversaturation as described in the example.

After an operating time of 4 days, operation had to be interrupted, since a Kanalrad pump used to charge the wash column with crystal suspension no longer brought about any delivery of the suspension S (blockage of line and/or pump).

U.S. Provisional Patent Application No. 60/971,994, filed Sep. 13, 2007, is incorporated into the present application by literature reference.

With regard to the abovementioned teachings, numerous changes and deviations from the present invention are possible. It can therefore be assumed that the invention, within the scope of the appended claims, can also be performed differently than the way described specifically herein.

The invention claimed is:

1. A process for continuously removing a target product X in the form of fine crystals of the target product X from a liquid phase P consisting of the target product X and constituents $B_i$ other than the target product X, whose total mole fraction of constituents $B_i$ has the value $M_{B,P}^{tot}$, comprising the operation of an indirect heat transferer having a secondary chamber and at least one primary chamber, in which the secondary chamber and the at least one primary chamber are each spatially separated from one another by at least one material dividing wall which serves as a surface for transfer of heat out of the secondary chamber into the at least one primary chamber, by conducting a stream of liquid phase P into the secondary chamber of the heat transferer, while the at least one primary chamber is simultaneously flowed through by at least one fluid cooling medium such that, in the secondary chamber, fine crystals of the target product X form from the liquid phase P to leave a liquid residual phase R, and are suspended in the remaining liquid residual phase R which, compared to the liquid phase P, comprises the constituents other than the target product X with a total mole fraction $M_{B,R}^{tot}>M_{B,P}^{tot}$ and whose content of target product X is at least 70% by weight to obtain a suspension S of fine crystals of the target product X in the liquid residual phase R which has a degree of crystallization Y, and suspension S with the temperature $T_S^{out}$ is withdrawn continuously from the secondary chamber of the heat transferer, and further comprising the supply of suspension S withdrawn with the temperature $T_S^{out}$ to a mixed buffer vessel, and, with the aid of a pump, the charging of a separating apparatus from the buffer vessel with suspension of fine crystals of the target product X present in the buffer vessel, and the separation of the suspension supplied to the separating apparatus into crystals present therein and liquid phase present therein, wherein, on the route from the secondary chamber into the buffer vessel, in the buffer vessel and/or in one or more pumped circulation lines leading out of the buffer vessel and back into it, the temperature of the suspension S fed to the buffer vessel is increased with the aid of an external energy source to a value $T^{Pu}$ above $T_S^{out}$ and/or the total mole fraction of the constituents other than the target product X which are present in the liquid residual phase R of the suspension S fed to the buffer vessel is increased to a value $M_{B,Pu}^{tot}$ above $M_{B,R}^{tot}$ by external addition of constituents other than the target product X.

2. The process according to claim 1, wherein $T^{Pu}-T_S^{out}$ is $\geq 0.1$ K.

3. The process according to claim 1, wherein the increase from $M_{B,R}^{tot}$ to $M_{B,Pu}^{tot}$, based on $M_{B,R}^{tot}$, is $\geq 0.1\%$.

4. The process according to any of claims 1 to 3, wherein the target product X is acrylic acid, methacrylic acid, N-vinylpyrrolidone or o-xylene.

5. The process according to any of claims 1 to 4, wherein the content in the liquid residual phase R of target product X is $\geq 80\%$ by weight.

6. The process according to any of claims 1 to 4, wherein the content in the liquid residual phase R of target product X is $\geq 90\%$ by weight.

7. The process according to any of claims 1 to 6, wherein the degree of crystallization Y is from 0.20 to 0.40.

\* \* \* \* \*